United States Patent
Narayan et al.

(10) Patent No.: US 8,217,193 B2
(45) Date of Patent: *Jul. 10, 2012

(54) MODIFIED FATTY ACID ESTERS AND METHOD OF PREPARATION THEREOF

(75) Inventors: Ramani Narayan, Okemos, MI (US); Daniel Graiver, Midland, MI (US); Kenneth W. Farminer, Midland, MI (US); Phuong T. Tran, Lansing, MI (US); Tam Tran, legal representative, Lansing, MI (US)

(73) Assignees: Board of Trustees of Michigan State University, East Lansing, MI (US); Bioplastic Polymers and Composites, LLC, Okemos, MI (US)

(*) Notice: Subject to any disclaimer, the term of this patent is extended or adjusted under 35 U.S.C. 154(b) by 68 days.

This patent is subject to a terminal disclaimer.

(21) Appl. No.: 12/584,914

(22) Filed: Sep. 15, 2009

(65) Prior Publication Data

US 2010/0084603 A1    Apr. 8, 2010

Related U.S. Application Data

(63) Continuation-in-part of application No. 11/363,101, filed on Feb. 27, 2006, now Pat. No. 7,589,222.

(60) Provisional application No. 60/656,678, filed on Feb. 28, 2005.

(51) Int. Cl.
    *C07C 51/16* (2006.01)
(52) U.S. Cl. ........................................ 554/133
(58) Field of Classification Search ............ 554/133
    See application file for complete search history.

(56) References Cited

U.S. PATENT DOCUMENTS

| | | | |
|---|---|---|---|
| 2,472,152 A | 6/1949 | Farkas et al. |
| 2,912,313 A | 11/1959 | Hinkamp et al. |
| 3,006,772 A | 10/1961 | Gerardus Martinus et al. |
| 3,112,329 A | 11/1963 | Pryde et al. |
| 3,350,336 A | 10/1967 | Kelley et al. |
| 3,647,759 A | 3/1972 | Walker |
| 3,929,730 A | 12/1975 | Graefe et al. |
| 3,993,576 A | 11/1976 | Barron |
| 4,048,104 A | 9/1977 | Svoboda et al. |
| 4,237,238 A | 12/1980 | DeGiuseppi et al. |

(Continued)

FOREIGN PATENT DOCUMENTS

BR    PI20005479-8    4/2002

(Continued)

OTHER PUBLICATIONS

International Search Report and the Written Opinion of the International Searching Authority dated Feb. 4, 2011, for Application No. PCT/US10/02477.

(Continued)

*Primary Examiner* — Deborah D Carr
(74) *Attorney, Agent, or Firm* — Dickinson Wright PLLC (57) ABSTRACT

A process for the preparation of new polyols and polyesters from a natural oil or other unsaturated fatty acid esters is described. The process involves ozone cleavage of double bonds in the fatty acid chains of the oils along with coupling of a hydroxylated compound such as a mono-alcohol, a diol, or a polyol to the cleaved ends of the molecules resulting from the cleavage with a base. The resulting polyols and polyesters are as intermediates for polymers.

22 Claims, 2 Drawing Sheets

U.S. PATENT DOCUMENTS

| | | | |
|---|---|---|---|
| 4,282,387 | A | 8/1981 | Olstowski |
| 4,314,088 | A | 2/1982 | Austin et al. |
| 4,326,047 | A | 4/1982 | Yates et al. |
| 4,346,229 | A | 8/1982 | Derr et al. |
| 4,416,747 | A | 11/1983 | Menth et al. |
| 4,468,233 | A | 8/1984 | Bruderreck et al. |
| 4,494,961 | A | 1/1985 | Venkat et al. |
| 5,001,292 | A | 3/1991 | Harandi et al. |
| 5,099,075 | A | 3/1992 | Katz et al. |
| 5,308,365 | A | 5/1994 | Kesling, Jr. et al. |
| 6,174,501 | B1 | 1/2001 | Noureddini |
| 6,433,121 | B1 | 8/2002 | Petrovic |
| 6,447,557 | B1 | 9/2002 | Yeh et al. |
| 6,488,727 | B2 | 12/2002 | Naegeli et al. |
| 6,673,230 | B2 | 1/2004 | Hagen et al. |
| 6,890,364 | B2 | 5/2005 | Delfort et al. |
| 7,367,995 | B2 | 5/2008 | Narayan et al. |
| 7,722,755 | B2 | 5/2010 | Lawson et al. |
| 2002/0000063 | A1 | 1/2002 | Yeh et al. |
| 2005/0262760 | A1 | 12/2005 | Lawson et al. |
| 2006/0194974 | A1* | 8/2006 | Narayan et al. ............... 554/133 |
| 2008/0202020 | A1 | 8/2008 | Narayan |
| 2008/0262259 | A1 | 10/2008 | Luo et al. |
| 2009/0176904 | A1 | 7/2009 | Narine et al. |

FOREIGN PATENT DOCUMENTS

| | | |
|---|---|---|
| DE | 3136030 | 3/1983 |
| EP | 0252606 | 1/1988 |
| JP | 50-052400 | 5/1975 |
| WO | 0249999 | 6/2002 |
| WO | WO2006/020716 A1 | 2/2006 |

OTHER PUBLICATIONS

Guo et al., Journal of Polym. & the Environ. 10: 49-52 (2002).

R.G. Ackman, M. E. Retson, L.R. Galley, and F.A. Vandenheuvel, Ozonolysis of Unsaturated Fatty Acids, Can. J. Chem. vol. 39, pp. 1956-1963 (Mar. 1961).

J.D. Castell and R.G. Ackman, Ozonolysis of Unsaturated Fatty Acids II. Esterification of the Total Products from the Oxidative Decomposition of Ozonides with 2,2-dimethoxypropane, Can. J. Chem vol. 45, pp. 1405-1410 (Jul. 1967).

Tran et al., JAOCS, vol. 82, No. 9, pp. 653-659, Sep. 2005.

Rheineck et al., JAOCS, vol. 46, pp. 452-454.

Dunn, R.O., "Effect of Oxidation Under Accelerated Conditions on Fuel Properties of Methyl Soyate (Biodiesel)," JAOCS, V. 79, N. 9, 2002, pp. 915-920.

Dunn, R.O., and Bagby, M.O., "Low-Temperature Phase Behavior of Vegetable Oil/Co-Solvent Blends as Alternative Diesel Fuel," JAOCS, V. 77, No. 12, 2000, pp. 1315-1323.

Yu, L., Lee, I., Hammond, E.G., Johnson, L.A., Van Gerpen, J.H., "The Influence of Trace Components on the Melting Point of Methyl Soyate," JAOCS, V. 75, N. 12, 1998, pp. 1821-1824.

PCT/US06/06863—Written Opinion of the International Searching Authority, dated Jul. 20, 2006, and International Publication No. 2006/093877, dated Sep. 8, 2006.

PCT/US06/06858—International Search Report and the Written Opinion of the International Searching Authority, dated Sep. 11, 2007.

* cited by examiner

MODIFIED FATTY ACID ESTERS AND METHOD OF PREPARATION THEREOF

CROSS REFERENCE TO RELATED APPLICATION

This application is a continuation-in-part of U.S. patent application Ser. No. 11/363,101, filed Feb. 27, 2006 (now U.S. Pat. No. 7,589,222), which in turn claims the priority benefit of U.S. Provisional Application No. 60/656,678, filed Feb. 28, 2005, both of which are incorporated herein by reference in their entireties.

BACKGROUND OF THE DISCLOSURE

1. Field of the Disclosure

The present invention relates to a process for producing a mixture of polyols and/or polyesters containing relatively higher molecular weight triglyceride- and/or fatty acid ester-based polyols and/or polyesters and relatively lower molecular weight linear polyols and/or polyesters. More specifically, the invention is related to such polyols and/or polyesters derived from bio-renewable resources including natural oils such as vegetable oils and animal oils.

2. Brief Description of Related Technology

Mixtures of polyols are commonly used in the manufacturing of polyurethane and polyester articles resulting from the reaction of liquid polyol mixtures and liquid isocyanates or carboxylates, respectively. Mixtures of primary hydroxyl terminated functional groups in polyols are desirable in commerce as they undergo rapid polymerization processes and their compositions greatly impact the physical properties of the polymeric articles. Commonly employed polyol mixtures consist of blends of low equivalent weight glycols such as ethylene glycol or 1,4-butanediol and primary hydroxyl terminated high molecular-weight polyether polyols. However, many such blends are incompatible fluids that tend to separate into layers on standing and thus, these blends should be constantly agitated to avoid a misformulation of the polymer because of the separation of components. Even more severe is the tendency of catalysts and other additive compounds in the blends to migrate into one of the phases and adversely impact the polymerization process. Recognition of this problem dictates that polyol blends containing low molecular weight polyols and high molecular weight polyols should be constantly agitated or alternatively a "chain extender" or a "solubilizer" should be employed.

A "chain extender" is disclosed by Graefe et al. in U.S. Pat. No. 3,929,730 issued Dec. 30, 1975 incorporated herein by reference in its entirety. This patent teaches the use of blends consisting of 1,4 butanediol with high molecular weight polyols having molecular weights of 2,000 or greater where a sufficient amount of phenylenediethanolamine is used as an extruder to render the mixture homogeneous. Similarly, a "solubilizer" derived from butylene glycol or propylene glycol is disclosed in U.S. Pat. No. 3,993,576 to Barron and is claimed to render the polyol mixture resistant to phase separations.

Olstowski and Nafziger in U.S. Pat. No. 4,282,387, issued Aug. 4, 1981, incorporated herein by reference in its entirety, disclosed the preparation of a mixture of polyether polyols by reacting alkylene oxides with hydroxyl initiator compounds in the presence of catalysts of calcium, strontium, or barium salts of organic acids. Although such catalysts need not be removed before the resultant product is used in the preparation of polyurethanes, they are generally available in a mineral spirit solvent which further contains monoether glycols that act as initiators. Consequently, mono functional species with respect to the hydroxyl group are present in the mixture and if their concentration is too high, they distract from the properties of the polymers when they are intended for high performance applications. Alternatively, Yates et al. in U.S. Pat. No. 4,326,047 discloses a process for preparing similar polyols mixtures using these catalysts wherein the catalyst is first precipitated from the mineral spirits carrier and the glycol ether coupling agent. The resulting catalyst is solid and thus, it must be re-dissolved in the reaction medium for it to be effective. This extra step takes time and negatively affects the productivity of the reaction and the polydispersity of the product prepared.

The vast majority of polyols are obtained from different petrochemical processes and are considered virgin polyols. Examples of such polyols include those prepared from terephthaloyl radicals as described in U.S. Pat. No. 3,647,759 to Walker; U.S. Pat. No. 4,237,238 to DeGiuseppi et al.; and U.S. Pat. No. 4,346,229 to Derr et al. It has also been disclosed that polyols can be obtained by chemical recycling processes for PET bottles as described in U.S. Pat. No. 4,048,104 to Svoboda et al. whereby pieces of poly(ethylene terephthalate) that is obtained from the collection of PET bottles are used to manufacture diethylene glycol and terephthaloyl radicals.

There are several known processes to chemically modified vegetable oils and produce triglycerides containing hydroxyl functional groups. One method to prepare polyols from various vegetable oils is described in Brazil Pedido PI (2002) Application: BR 2000-5479 20001016 by Calderon Velasco, Rodrigo. It is based on transesterification of the fatty acids in the triglycerides with a polyol such as glycerin, trimethylolpropane, pentaerythritol, sorbitol, amino-alcohols, glycols including ethylene glycol, propylene glycol, diethylene glycol, and neopentyl glycol. Other hydroxylated compounds such as pentaerytol, α-methylglucoside or sucrose are also suitable. Unfortunately, premature degradation occurs by this process due to high temperatures (200-240° C.) and a relatively long period of time in the tranesterification reaction. Furthermore, the resulting product distribution contains only glycerides and no low molecular weights linear polyols.

Another method described in U.S. Pat. No. 6,433,121, to Petrovic is based on a consecutive two-step process involving epoxidation and then hydroxylation of vegetable oils with peroxyacid to yield polyol mixtures. According to this method, the epoxide rings are open or hydroxylated with polyfunctional alcohols to yield secondary alcohols. Although epoxidized soy oil is available commercially, the reactivity of this oil is low since only secondary alcohols are obtained and these are inherently less reactive than primary alcohols. Furthermore, several hydroxyl groups per fatty acid residue are obtained by this route (at least these fatty acids that contain more than one double bond). Consequently, multiple numbers of hydroxyl groups having varying reactivity are present, which tend to complicate subsequent reactions and can even lead to premature gelation. These polyols have also been shown to exhibit poor functionality and thus, they must be mixed with other high functionality polyols so that when polymerized, sufficient cross-linking is achieved.

Hydroformylation of vegetable oils offers another method to prepare polyols described by Guo et al. in the *J. of Polym. and the Environ.* 10: 49-52 (2002). According to this method, an aldehyde functional vegetable oil is first obtained, which is then hydrogenated to alcohols. Polyurethanes prepared from these polyols had different mechanical properties depending on the hydroformylation catalyst that was used. Thus, rigid materials at room temperature were obtained with a rhodium catalyst while a cobalt catalyzed hydroformylation led to rubbery materials.

An alternative method for preparing primary polyols is based on oxidizing an olefin having a carbonyl group with molecular oxygen followed by hydrolysis and reduction of the acetal (or ketal) to an alcohol is described by Takahara, J. et al. in WO Application Patent 2002049999 (2002). This method is much more complicated and must run at high pressure and thus, is not very economical.

Another method described by Austin et al. in U.S. Pat. No. 4,314,088 is based on an oxidation process of the olefinic compounds to yield polyols using an organic hydroperoxide in the presence of $OsO_4$ and a NaBr co-catalyst. However, the use of toxic heavy metals requires careful operation and disposal protocols of the waste heavy metal residue, which render this method not very practical. Another oxidation process employs ozone to cleave and oxidize the double bonds in the vegetable oil and then reduce the decomposing ozonides to alcohols using $NaBH_4$ or similar reducing agents. Although the oxidation and cleavage of the double bonds are fast and effective, the subsequent reduction process is costly and not very useful commercially.

It is apparent from the foregoing that although polyols derived from various starting materials by a variety of processes have been disclosed, they either exhibit low levels of compatibility or are not sufficiently reactive or are not useful in the polymerization of polyurethanes and polyesters. Moreover, all the polyol mixtures obtained from vegetable or animal oils without complete cleavage of the double bonds are composed of relatively high molecular weight glyceride derivatives whereby complete cleavage of the double bonds in these oils lead to an unstable polyol mixture.

Objects

It is therefore an object of the present invention to provide a mixture of polyols derived from raw materials that come from a source other than petroleum, since this is not renewable.

Another object of this invention is to provide a mixture comprising low molecular weight linear polyols and high molecular weight triglyceride functional polyols that is stable and does not phase separate upon standing or during the polymerization process.

An additional object of this invention is to provide a process for obtaining oleochemical primary polyols. The process is efficient, relatively simple and readily facilitates the conversion of raw materials into products.

Yet another object of the present invention is to provide a process for obtaining highly reactive primary polyols suitable for producing different types of polyurethane and polyester articles such as resins, coatings, elastomers, foams, etc. Such polyester polyols allow the preparation of these articles with no need to supplement the mixture with other polyols.

An additional object of the present invention is to provide a process for obtaining polyols that provide high degrees of cross-linking in said articles by the high functionality of the polyols mixture.

These and other objects may become increasingly apparent by reference to the following description.

SUMMARY

It has been discovered that blends of polyols by the present invention are single-phase liquid mixtures although they are composed of low equivalent weight linear hydroxyl functional radicals and high equivalent weight triglycerides primary capped polyols. The processing method is based on a catalytic ozonation whereby the double bonds of the unsaturated fatty acid residues are cleaved and reacted with a polyol in a one-step process to produce primary alcohol functional groups.

It is desirable to employ suitable polyols from renewable resources, such as natural oils including vegetable oils and animal oils, instead of petroleum-based chemicals. In addition to being environmentally friendly, natural oils are a stable source of materials that is readily available and which can be produced by less costly processes than petroleum-based polyols.

The present invention addresses the need to produce primary polyols suitable in these polymerizations by chemical modifications of natural (vegetable, animal) oils. The catalytic oxidation process synthesizes polyol blends that are self-compatible and do not phase-separate on standing or during the polymerization process.

The invention provides a stable mixture of high and low molecular weight polyester polyols prepared by catalytic ozonation of vegetable oil containing unsaturated fatty acids in the presence of a hydroxylated compound. This primary polyol mixture is obtained by exposing the oil to ozone in the presence of an alkaline catalyst and an alcohol having two or more hydroxyl groups. The reaction can be run with no solvent or in a solvent or dispersant which is not affected by the ozone. The polyester polyols mixture thus prepared is composed of hydroxyl functional triglycerides and low molecular weight, linear polyols. The particular composition of the polyol mixture depends on the type of oil and more specifically on the type and amount of the unsaturated fatty acids in the triglycerides. Thus, ozonation and cleavage of linoleic acid radical on a triglyceride in the presence of ethylene glycol will yield 2-hydroxyethyl nonanoate radical on the triglyceride and the linear (2-hydroxylethyl) hexanoate and bis(2-hydroxylethyl) malonate fragments.

The disclosure relates to a method for making a modified fatty acid ester. The method comprises: (a) reacting an unsaturated fatty acid ester with ozone in a reaction mixture in the presence of a hydroxylated compound and an alkaline catalyst to form a reaction product, wherein: (i) the ozone and the unsaturated fatty acid ester react to cleave double bonds in fatty acid groups of the unsaturated fatty acid ester, and (ii) the hydroxylated compound, in the presence of the alkaline catalyst, is added to terminal carbons of the cleaved double bonds through an ester covalent bond. In another embodiment, disclosure relates to a method of making a natural oil-based primary polyol, the method comprising ozonizing a natural oil in the presence of a polyol and an alkaline catalyst.

The disclosure also relates to a composition derived from a fatty acid ester (e.g., a reaction product of the foregoing methods). The composition comprises: (a) a modified fatty acid ester comprising: an ester of an alkaline-catalyzed, ozone-cleaved unsaturated fatty acid ester comprising a terminal carbon atom, wherein the terminal carbon atom is covalently linked through an ester reaction product of (i) the alkaline-catalyzed, ozone-cleaved unsaturated fatty acid and (ii) the hydroxylated compound.

Various embodiments of the foregoing methods and compositions are possible, The unsaturated fatty acid ester can include a natural oil triglyceride such as an animal oil triglyceride (e.g., one or more of fish oil, tallow (beef, mutton), lard, suet (beef, mutton), neatsfoot oil, bone oil, and butter oil) The unsaturated fatty acid ester also can include a natural oil triglyceride such as a vegetable oil triglyceride (e.g., one or more of soybean oil, safflower oil, linseed oil, corn oil, sunflower oil, olive oil, canola oil, sesame oil, cottonseed oil, palm oil, peanut oil, coconut oil, rapeseed oil, tung oil, castor oil, almond oil, flaxseed oil, grape seed oil, olive oil, safflower oil, sunflower oil, and walnut oil). Alternatively or additionally, the unsaturated fatty acid ester can comprise a monoester of an unsaturated fatty acid residue (e.g., having from 10 to 24 carbon atoms). When the unsaturated fatty acid ester includes a triglyceride, the resulting modified fatty acid ester can include more than three (or more than four) ester groups per triglyceride molecule. The hydroxylated compound can have at least two hydroxyl groups (e.g., one or more of glycols, linear polyols, glycerin, trimethylol propane, pentaerythritol, glucosides, sugars, and catechols; one or more of ethylene glycol, 1,2-propylene glycol, 1,3-propylene glycol, 1,2-butylene glycol, 1,3-butylene glycol, 1,4-butylene glycol, 1,2-pentylene glycol, 1,3-pentylene glycol, 1,4-pentylene glycol, 1,5-pentylene glycol, neopentyl glycol, and hexane diols; such that the resulting modified fatty acid ester comprises primary alcohol groups). Alternatively or additionally, the hydroxylated compound can comprise a mono-alcohol (e.g., one or more of a linear hydrocarbon chain, a branched hydrocarbon chain, and combinations thereof; one or more of methanol, ethanol, propanol, isopropanol, a linear alkyl mono-alcohol having 4 to 10 carbon atoms, and a branched alkyl mono-alcohol having 4 to 10 carbon atoms). The alkaline catalyst can comprise one or more of an alkali metal hydroxide, an organic amine, a salt derived from a strong base and a weak acid, and a metal oxide having an alkaline surface. The composition or reaction product can additionally include one or more of diesters and monoesters resulting from the reaction of the hydroxylated compound with cleaved portions of the fatty acid groups of the fatty acid ester. Alternatively, the composition or reaction product can be purified to separate the diesters and/or monoesters (e.g., low molecular weight compounds are removed to provide a low-volatile composition or reaction product, such as one consisting (essentially) of the modified fatty acid ester).

Figure 1:
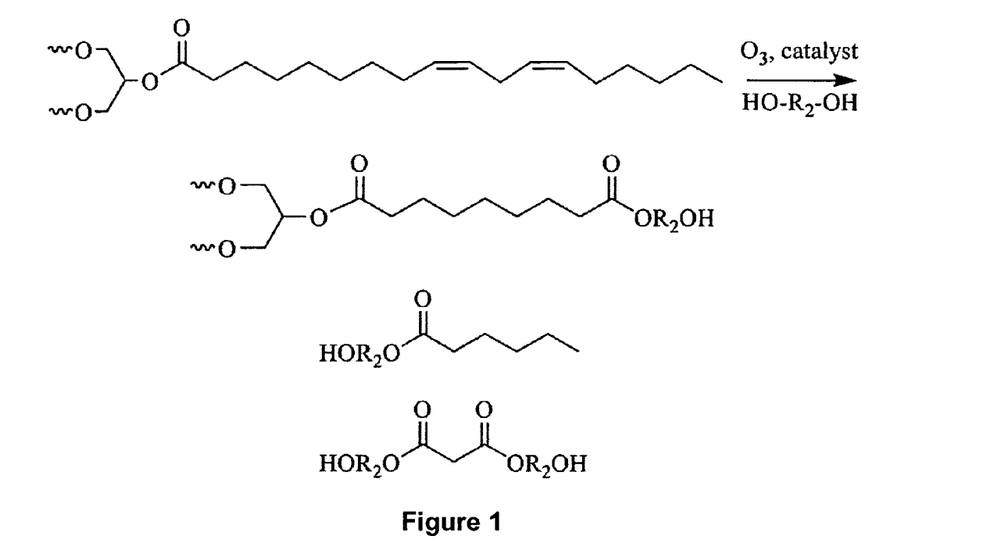
FIG. 1 illustrates an ozonation reaction according to the disclosure of a triglyceride having a linoleic fatty acid residue with a hydroxylated compound having two hydroxyl groups.
Figure 2:
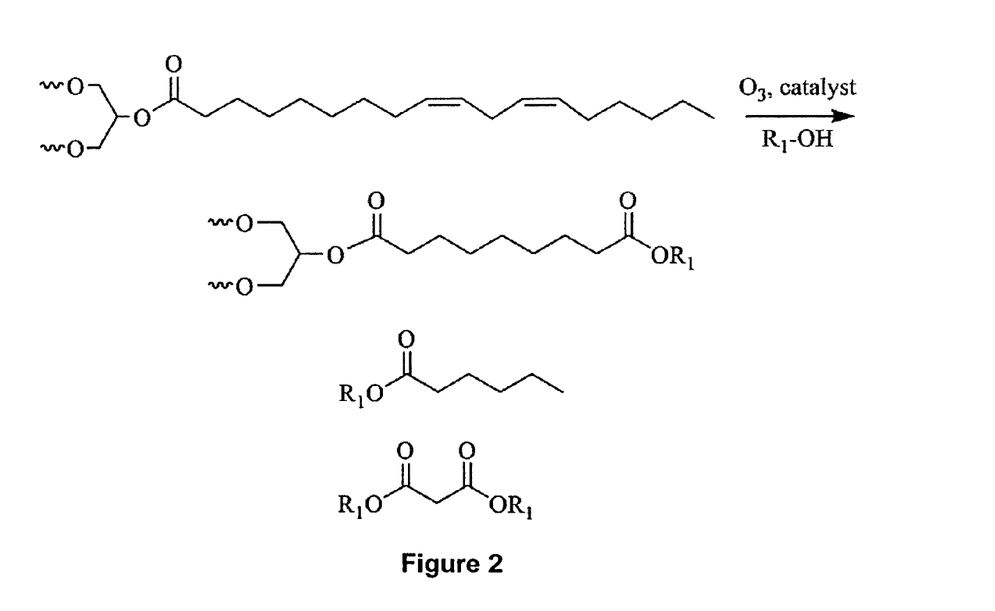
FIG. 2 illustrates an ozonation reaction according to the disclosure of a triglyceride having a linoleic fatty acid residue with a hydroxylated compound having one hydroxyl group.
Figure 3:
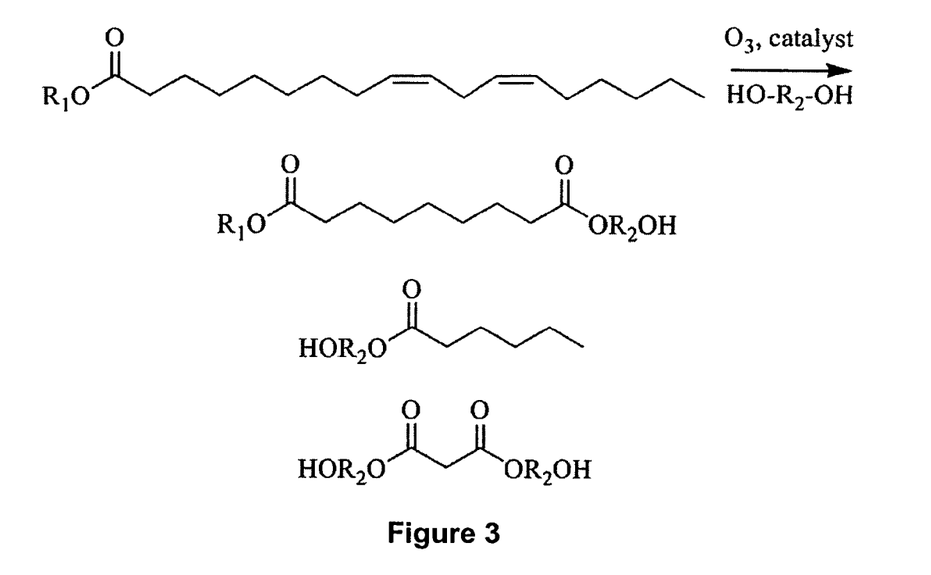
FIG. 3 illustrates an ozonation reaction according to the disclosure of a linoleic fatty acid monoester with a hydroxylated compound having two hydroxyl groups.
Figure 4:
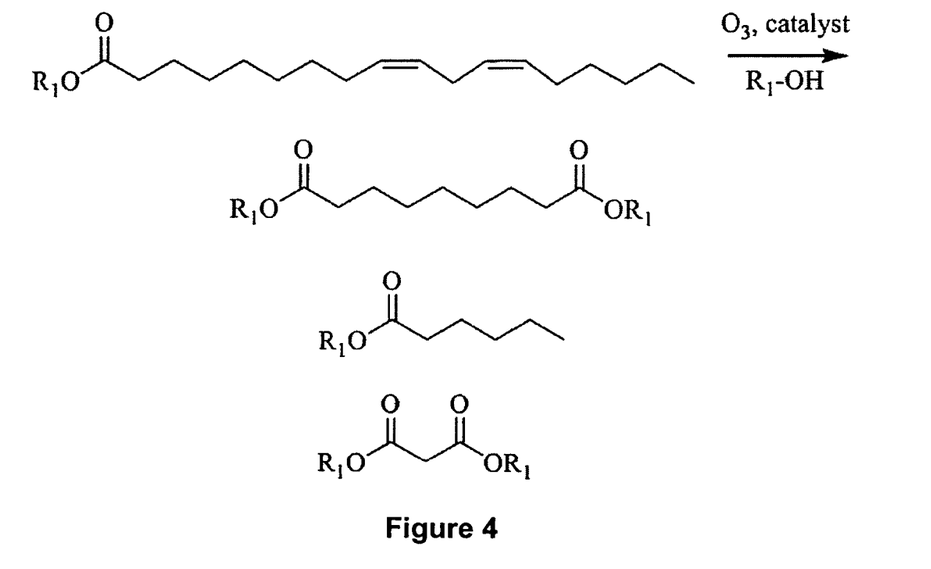
FIG. 4 illustrates an ozonation reaction according to the disclosure of a linoleic fatty acid monoester with a hydroxylated compound having one hydroxyl group.

FIGS. 1-4 illustrate the foregoing methods, reaction products, and compositions based on the particular selection of the unsaturated fatty acid ester and the hydroxylated compound. FIGS. 1-4 each illustrate an unsaturated fatty acid ester including a linoleic acid residue as the particular unsaturated fatty acid residue; however, any unsaturated fatty acid residue is suitable and yields analogous reaction products. In FIG. 1, the unsaturated fatty acid ester is a triglyceride and the hydroxylated compound contains two hydroxyl groups (e.g., an alkylene group $R_2$ with two —OH groups). The resulting cleaved, modified triglyceride includes a primary alcohol group (and possibly two or three alcohol groups, if the original triglyceride contains two or three unsaturated fatty acid residues, respectively). Modified triglyceride-based polyols can be used a polymer precursor, while modified triglyceride-based mono-alcohols (e.g., from triglycerides containing only one unsaturated fatty acid reside) can be used as a plasticizer or a polymer chain terminator. In FIG. 2, the unsaturated fatty acid ester is a triglyceride and the hydroxylated compound is a mono-alcohol (e.g., an alkyl alcohol $R_1$—OH). The resulting cleaved, modified triglyceride includes an additional ester group (i.e., beyond the base three ester groups a triglyceride), possibly including two or three additional ester groups, if the original triglyceride contains two or three unsaturated fatty acid residues, respectively. The polyester products can be used in polyester production (e.g., to increase the bio-based content thereof). The polyester products are suitable for polycondensation reactions. Specifically, these bio-based esters and di-esters can be homopolymerized to yield polyesters by transesterification with diols. These diols can further be transesterified with exsiting polyesters to increase the bio-based content of the resulting copolymers. In FIG. 3, the unsaturated fatty acid ester is a monoester and the hydroxylated compound contains two hydroxyl groups (e.g., an alkylene group $R_2$ with two —OH groups). The mono-alcohol products can be used as reactive plasticizers or to control the molecular weight (e.g., a mono-functional terminating moiety) of a polyol-based polymer in a subsequent polymerization process. The diol products can be used in polyester production. In FIG. 4, the unsaturated fatty acid ester is a monoester and the hydroxylated compound is a mono-alcohol (e.g., an alkyl alcohol $R_1$—OH). The polyester products can be used in polyester production (e.g., to increase the bio-based content thereof) in a manner similar to that described with respect to the reaction products illustrated in FIG. 2.

In another embodiment, the invention is a process for preparing such mixtures of primary polyester polyols. The process comprises first, contacting a vegetable oil containing unsaturated fatty acid triglycerides with compounds having two (2) or more hydroxyl groups in the presence of an alkaline catalyst. The mixture is exposed to ozone at temperatures between room temperature and the freezing point of the oil for sufficient periods of time to allow the ozone to react with the unsaturated compounds. Under these conditions, the double bonds are cleaved and the new terminal ends are reacted with the hydroxyl compound through a new ester linkage.

The present invention relates to a composition derived from a vegetable oil comprising triglycerides having multiple ester linkages with more than three ester groups per glyceride group. Further, the present invention relates to a method for making a modified triglyceride which comprises: reacting vegetable oil with ozone in a reaction mixture in the presence of a hydroxylated compound and alkaline catalyst wherein the ozone and the vegetable oil react to cleave double bonds in fatty acid groups of the triglyceride, wherein the hydroxylated compound, in the presence of the catalyst, is added to terminal carbons of the cleaved double bonds through an ester covalent bond. Further, the present invention relates to a composition where additional diesters and mono-esters are present from the reaction of the hydroxylated compound with the cleaved portions of fatty acid groups not linked to the triglyceride. Still further, the present invention relates to a composition wherein the hydroxylated compound is selected from the group consisting of a mono-alcohol and mixtures thereof. Preferably, the invention relates to a composition wherein the hydroxylated compound is selected from the group consisting of polyols and mixtures thereof. Most preferably, the invention relates to a composition wherein the hydroxylated compound is selected from the group consisting of alcohol composed of hydrocarbon chains and mixtures thereof. Further, the invention relates to a composition wherein the hydroxylated compound is selected from the group consisting of an alcohol containing heteroatoms and mixtures thereof. Still further, the invention relates to a composition wherein the hydroxylated compound is selected from the group consisting of a linear, branched, hyperbranched, or dendritic alcohol and mixtures thereof. Further still, the invention relates to a composition wherein the vegetable oil consists of triglycerides containing unsaturated double bonds.

Preferably, the invention relates to a composition wherein the vegetable oil is selected from the group consisting of triglycerides derived from soybean oil, safflower oil, linseed oil, corn oil, sunflower oil, olive oil, canola oil, sesame oil, cottonseed oil, palm oil, peanut oil, coconut oil, rapeseed oil, tung oil, castor oil, fish oil and mixtures thereof. Most preferably, the invention relates to a composition containing primary alcohols derived from the reaction of the triglycerides and the hydroxylated compound. Still further, the invention relates to a composition wherein a hydroxyl number is between 0.5 and 5.0. Further still, the invention relates to a composition containing primary amine groups derived from the reaction of said triglycerides and amino alcohols as the hydroxylated compound. Still, the invention relates to a composition wherein any low molecular weight compounds are removed from the composition to yield a low volatile composition. Further, the invention relates to a composition wherein solvent, antifoam agents, rheology modifiers, inorganic filler, and other additives, reactants or process aids are present. Further still, the invention relates to a composition consisting essentially of the reaction mixture without purification. Still further, the invention relates to a method wherein ozone is derived from an oxygen containing atmosphere. Further, the invention relates to a method wherein an alcohol is used as a solvent.

Preferably, the invention relates to a process wherein the said catalyst is an alkaline compound selected from the group consisting of: (a) a base; (b) an amine; (c) a metal oxide; and (d) mixtures thereof. Most preferably, the invention relates to a method wherein the catalyst is soluble in the reaction mixture. Further, the invention relates to a method wherein the catalyst is insoluble in the reaction mixture. Still further, the invention relates to a method of making a vegetable oil-based primary polyol comprising ozonizing a vegetable oil in the presence of a polyol and the catalyst.

All patents, patent applications, government publications, government regulations, and literature references cited in this specification are hereby incorporated herein by reference in their entirety. In case of conflict, the present description, including definitions, will control.

Additional features of the disclosure may become apparent to those skilled in the art from a review of the following detailed description, taken in conjunction with the examples and appended claims, with the understanding that the disclosure is intended to be illustrative, and is not intended to limit the claims to the specific embodiments described and illustrated herein.

BRIEF DESCRIPTION OF THE DRAWINGS

For a more complete understanding of the disclosure, reference should be made to the following detailed description and accompanying drawings wherein.

While the disclosed compositions and methods are susceptible of embodiments in various forms, specific embodiments of the disclosure are illustrated in the drawings (and will hereafter be described) with the understanding that the disclosure is intended to be illustrative, and is not intended to limit the claims to the specific embodiments described and illustrated herein.

DETAILED DESCRIPTION

The stable polyester-polyols mixtures of the invention are generally prepared by contacting ozone gas with a natural oil such as a vegetable oil or an animal oil in the presence of alcohol radicals (e.g., containing two or more hydroxyl groups) and an alkaline catalyst under appropriate conditions for the unsaturated bonds to cleave and to add to the alcohol at the new terminal chain ends.

The use of ozone to cleave organic double bonds is well known to those skilled in the art. Ozone is a very powerful oxidation agent and it readily attacks and cleaves double bonds in alkenes. Aside from its high oxidation potential, ozone oxidation is convenient since unreacted ozone simply decomposes back to oxygen and no special neutralization or separation are required at the end of the reaction. Furthermore, since ozone is being produced "on site" it does not require complex logistics in transport, storage and disposal as many other oxidation agents. However, unlike uncatalyzed ozonation that yields a mixture of aldehyde and ketones functional radicals, the alkaline catalyzed ozonation, in accordance with our invention, results in the formation of ester linkages between the alcohol and the new chain ends of the cleaved double bonds.

Any natural oil such as a vegetable oil or an animal oil may be used in this process. Natural oils generally include any fatty acid triglyceride derived from a natural source (e.g., plants (vegetables), animals). Examples of such oils that may be used include, but are not limited to, soybean oil, safflower oil, linseed oil, corn oil, sunflower oil, olive oil, canola oil, sesame oil, cottonseed oil, palm oil, peanut oil, coconut oil, rapeseed oil, tung oil, castor oil, almond oil, flaxseed oil, grape seed oil, olive oil, safflower oil, sunflower oil, walnut oil, fish oil, tallow (beef, mutton), lard, suet (beef, mutton), blubber oil, neatsfoot oil, bone oil, butter oil or any mixtures thereof. Additionally, any partially hydrogenated vegetable oils or genetically modified vegetable oils can also be used. Examples of partially hydrogenated vegetable oils or genetically modified vegetable oils include, but are not limited to, high oleic safflower oil, high oleic soybean oil, high oleic peanut oil, high oleic sunflower oil and high erucic rapeseed oil (crambe oil). The natural oils have at least some degree of unsaturation in their fatty acid residues to promote the catalyzed ozonation reaction with the hydroxylated compound. The natural oil fatty acid triglycerides can be characterized in terms of the average ratio of unsaturated fatty acid residues (i.e., a fatty acid residue with at least one carbon-carbon double bond) to saturated fatty acid residues (i.e., an average based on the distribution of fatty acid residues in an ensemble of triglyceride molecules). For example, fatty acid triglycerides suitably have an unsaturated:saturated ratio (or "degree of unsaturation") of at least about 1, 1.5, 2, 3, or 5 and/or up to about 8, 10, or 15. While some animal oils typically have degrees of unsaturation of about 1 (e.g., tallow, lard), animals raised on feedstocks having relatively high degrees of saturation (e.g., soybeans/soybean oil) can provide animal oils with increased degrees of unsaturation that may be used in the disclosed methods/compositions. Alternatively, any fatty acids or fatty ester containing unsaturation in their structure, either individually or as mixtures, can also be used. Suitable fatty acids and fatty acid residues (e.g., a fatty acid less its terminal acidic hydrogen, such as when in the form of an ester) include those with 10 to 24 carbon atoms, 16 to 20 carbon atoms, or 18 carbon atoms (e.g., oleic, linoleic, and/or linolenic fatty acids and residues). The fatty acid esters can include triesters (e.g., triglycerides of the fatty acids, prior to ozonation), diesters (e.g., diglycerides and other esters of the fatty acids and the polyols described herein, prior to ozonation), and monoesters (e.g., monoglycerides and other esters of the fatty acids and the mono-alcohols and polyols described herein, prior to ozonation). The iodine values of these vegetable oils range from about 40 to 240 and more preferably from about 80 to 240. When vegetable oils having lower iodine values are used to make vegetable oil-based polyols, polyols with lower hydroxyl numbers are obtained.

Preferable hydroxylated compounds, which are employed to prepare the polyester polyols (illustrated in FIG. 1) and linear ester-alcohols (illustrated in FIG. 3), are organic compounds having at least two (2) active hydrogens (i.e., at least two hydroxyl (—OH) groups). Preferred compounds include but are not limited to glycols, linear polyols, glycerin, trimethylol propane, pentaerythritol, glucosides, sugars, catechols, and the like. Particularly, suitable glycols include ethylene glycol, 1,2-propylene glycol, 1,3-propylene glycol, 1,2-butylene glycol, 1,3-butylene glycol, 1,4-butylene glycol, 1,2-pentylene glycol, 1,3-pentylene glycol, 1,4-pentylene glycol, 1,5-pentylene glycol, neopentyl glycol and various hexane diols, mixtures thereof and the like.

The hydroxylated compounds additionally or alternatively can include mono-alcohols (i.e., having one hydroxyl (—OH) group). Mono-alcohols having a hydrocarbon chain and one hydroxyl group are employed to form mono-, di-, and polyester compounds, as illustrated in FIGS. 2 and 4. The mono-alcohol can have a linear hydrocarbon chain, a branched hydrocarbon chain, or can be a mixture of linear and branched alcohols. Suitable mono-alcohols include methanol, ethanol, propanol, isopropanol, and other alkyl mono-alcohols (e.g., linear or branched, having 4-10 carbon atoms, and/or having 4-6 carbon atoms).

The catalysts used in preparing the polyester-polyols mixture of this invention are solid or liquid alkaline compounds. Examples of such catalysts include but are not limited to alkali metal hydroxides (such as LiOH, NaOH, KOH and CsOH), organic amines (such as butyl amine, diethyl amine, pyridine, or 4-dimethylamino-pyridine), various salts derived from a strong base and a weak acid (such as calcium carbonate and magnesium carbonate), compounds composed of metal oxides having alkaline surface (such as MgO). The salt catalysts may be prepared by contacting the appropriate ratio of a strong base such as calcium hydroxide with a $C_{6-10}$ carboxylic acid and bubbling carbon dioxide through the mixture to form carbonate moieties. The catalysts suitable for this invention can either be soluble in the reaction mixture, known in the art as homogeneous catalyst or it can be dispersed as fine particles known as heterogeneous catalyst.

The concentration of the catalyst depends on the alkalinity of the particular catalyst used and the experimental conditions of the reaction. Thus, provided that a soluble and strong alkaline catalyst like NaOH is used, a concentration of 0.1 to 1.0 wt. % is sufficient when the reaction temperature is between 0° C. and 25° C., an ozone/oxygen flow rate of 0.25 ft$^3$/min is used and the concentration of ozone in the gas atmosphere is about 6%. When a heterogeneous catalyst is used, the average particle size and the particle size distribution must also be considered as smaller particles provide a higher total surface area than identical concentrations of the catalyst with larger particles. The amount of catalyst is therefore adjusted to provide maximum formation of ester linkages between the alcohol radicals and the new chain ends that are formed as a result of the cleavage of the double bonds as a result of the ozone attack.

Soluble (homogeneous) catalysts are neutralized at the end of the reaction with acidic compounds such as acetic acid, carbon dioxide and the salt is then separated from the product by washing with water and separating the desired oil phase from the water phase. When heterogeneous catalyst is used and it is dispersed in the reaction mixture as fine particles or present as a separate phase, the product is purified simply by filtration of the catalyst phase and removing it from the reaction product. In this case, the recovered catalyst can be re-used.

Solvents or dispersants are not needed but can be used to control the viscosity of the reaction mixture or to enhance the compatibility of the various components in the reaction mixture. Such solvents or dispersants can be mineral spirits, silicone oil or chlorinated organic compounds commonly used in ozonolysis reaction. Preferably the solvent should be stable to ozone and does not have unsaturation. In a preferred embodiment, no solvent or dispersant is used. However, a solvent may be desirable when the unsaturated fatty acid ester would otherwise be a solid at reaction (or ambient) temperatures (e.g., a natural oil triglyceride, such as some animal oil triglycerides, that is not (completely) solvated by the particularly selected hydroxylated compound in the reaction mixture). A solvent additionally may be desirable when the hydroxylated compound is relatively insoluble in the reaction mixture (e.g., sugars or glucosides in natural oils). Alternatively, a reaction mixture containing unsaturated fatty acid esters and/or hydroxylated compounds that are otherwise insoluble in the reaction mixture can be processed under high shear (e.g., to disperse and mix insoluble components throughout the reaction mixture).

Examples of alcohols or alcohol mixtures that may be used in the reaction include, but are not limited to, glycols such as ethylene glycol, 1,2-propylene glycol, 1,3-propylene glycol, 1,2-butylene glycol, 1,3-butylene glycol, 1,4-butylene glycol, 1,2-pentylene glycol, 1,3-pentylene glycol, 1,4-pentylene glycol, 1,5-pentylene glycol, neopentyl glycol and various hexane diols and mixtures thereof. Other alcohols including low molecular weight polyols, glycerin, trimethylol propane, pentaerythritol, glucosides, sugars, catechols, and the like are also appropriate and can be used. Suitable mono-alcohols include methanol, ethanol, propanol, isopropanol, and other linear or branched alkyl mono-alcohols (e.g., having 4-10 or 4-6 carbons). Preferably, the alcohol used in the hydroxylation reaction has multiple hydroxyl groups and is miscible in the reaction mixture under the process conditions. It is important to employ an excess amount of alcohol during the hydroxylation step so as to prevent side reactions that will degrade from the purity of the desired polyol product. Typical side reactions are known to those skilled in the art and include polymerization, cross-linking, and the formation of products having higher viscosities.

The catalytic ozonation reaction occurs at approximately room temperature or between about 0° C. and 30° C. During the introduction of ozone, the temperature of the reaction can rise and therefore cooling should be applied. The extent to which the temperature rises depends upon the rate of the reaction, the temperature of the ozone/gas mixture, and the presence of solvent. The temperature can be controlled and maintained by contacting the reaction vessel with ice, coolant, or any other cooling methods familiar to the person expert in the art. It is preferable to maintain the reaction temperature close to 0° C. for safety as a balance between the solubility of ozone in the reaction medium and the rate of the reaction.

In a typical process, ozone is produced by passing dry oxygen (0.25 ft$^3$/min) through an ozone generator (Praxair Trailigaz generator model number OZC-1001), Cincinnati, Ohio, set up to yield about 6 wt. % ozone in oxygen. This ozone/oxygen atmosphere is introduced into the reaction medium as small gas bubbles by passing the gas stream through a fritted disc having fine pores. The formation of these small gas bubbles improved the dispersion of ozone within the reaction medium. The dispersion of the fine gas bubbles is further improved by stirring the reaction mixture using a mechanical stirrer equipped with an appropriate stirrer. Any unreacted ozone that escaped from the reaction without reacting with the oil is destroyed by venting it through an exhaust outlet and into an aqueous potassium iodide solution.

This method for making vegetable oil-based polyols is illustrated in the following Examples. Similar methods may be used for other unsaturated fatty acid ester (e.g., including other natural oil triglycerides) and/or mono-alcohol reactants. These Examples are not meant in any way to limit the scope of this invention.

EXAMPLES

Example 1

Soybean oil (200 g), ethylene glycol (150 g) and $CaCO_3$ (20 gr) were placed in a 500 mL glass reactor and maintained at 0° C. in an ice/water bath under continuous stirring. Ozone was produced by passing oxygen through the Praxair Trailigaz OZOBLOC Model OZC-1001 ozone generator. The operating conditions of the generator were set to produce an atmosphere containing 6-10 wt % ozone at 12 psi that was fed into the reactor through the fritted disc as small bubbled at a flow rate of 0.35 $ft^3$/min. The exhaust outlet from the reactor was connected to a potassium iodide aqueous solution trap in order to destroy excess ozone that has not been reacted. After 50 minutes reaction time, the ozone generator was switched off, the reaction mixture was allowed to warm up to room temperature and then washed with about 500 mL distilled water to remove any excess unreacted ethylene glycol. The $CaCO_3$ catalyst was then filtered out through a fine filter paper and the product was dried over molecular sieves for 48 hours.

The product mixture was characterized by FTIR and NMR and the results indicate that 27.5% of the double bonds have been cleaved. Hydroxyl functionality, defined here as the average number of hydroxyl groups in 1 mole of triglyceride was derived from the hydroxyl number (defined according to ASTM test method D1957-86 as the number of mg of potassium hydroxide equivalent to acetic anhydride consumed in the acetylation of 1 g of sample) was 0.25. The polyol product mixture was stable for 1 month at room temperature and no visible phase separation was observed.

Example 2

Soybean oil (200 g), ethylene glycol (150 g) and $CaCO_3$ (20 gr) were placed in a 500 mL glass reactor and maintained at 0° C. in an ice/water bath under continuous stirring. Ozone was produced as described in Example 1 and was fed into the reactor through the fritted disc as small bubbles at a flow rate of 0.35 $ft^3$/min. The exhaust outlet from the reactor was connected to a potassium iodide aqueous solution trap in order to destroy excess ozone that has not been reacted. After 100 minutes reaction time, the ozone generator was switched off, the reaction mixture was allowed to warm up to room temperature and then washed with about 500 mL distilled water to remove any excess unreacted ethylene glycol. The $CaCO_3$ catalyst was then filtered out through a fine filter paper and the product was dried over molecular sieves for 48 hours.

The product mixture was characterized by FTIR and NMR and the results indicate that 40% of the double bonds have been cleaved. Hydroxyl functionality, defined here as the average number of hydroxyl groups in 1 mole of triglyceride, was derived from the hydroxyl number (defined according to ASTM test method D1957-86 as the number of mg of potassium hydroxide equivalent to acetic anhydride consumed in the acetylation of 1 g of sample) was 2.6. The polyol product mixture was stable for 1 month at room temperature and no visible phase separation was observed.

Example 3

Soybean oil (200 g), ethylene glycol (150 g) and $CaCO_3$ (20 gr) were placed in a 500 mL glass reactor and maintained at 0° C. in an ice/water bath under continuous stirring. Ozone was produced as described in Example 1 and was fed into the reactor through the fritted disc as small bubbles at a flow rate of 0.35 $ft^3$/min. The exhaust outlet from the reactor was connected to a potassium iodide aqueous solution trap in order to destroy excess ozone that has not been reacted. After 200 minutes reaction time, the ozone generator was switched off, the reaction mixture was allowed to warm up to room temperature and then washed with about 500 mL distilled water to remove any excess unreacted ethylene glycol. The $CaCO_3$ catalyst was then filtered out through a fine filter paper and the product was dried over molecular sieves for 48 hours.

The product mixture was characterized by FTIR and NMR and the results indicate that 66% of the double bonds have been cleaved. Hydroxyl functionality, defined here as the average number of hydroxyl groups in 1 mole of triglyceride, was derived from the hydroxyl number (defined according to ASTM test method D1957-86 as the number of mg of potassium hydroxide equivalent to acetic anhydride consumed in the acetylation of 1 g of sample) was 4.5. The polyol product mixture was stable for 1 month at room temperature and no visible phase separation was observed.

Example 4

Soybean oil (200 g), ethylene glycol (150 g) and $CaCO_3$ (20 gr) were placed in a 500 mL glass reactor and maintained at 0° C. in an ice/water bath under continuous stirring. Ozone was produced as described in Example 1 and was fed into the reactor through the fritted disc as small bubbles at a flow rate of 0.35 $ft^3$/min. The exhaust outlet from the reactor was connected to a potassium iodide aqueous solution trap in order to destroy excess ozone that has not been reacted. After 400 minutes reaction time, the ozone generator was switched off, the reaction mixture was allowed to warm up to room temperature and then washed with about 500 mL distilled water to remove any excess unreacted ethylene glycol. The $CaCO_3$ catalyst was then filtered out through a fine filter paper and the product was dried over molecular sieves for 48 hours.

The product mixture was characterized by FTIR and NMR and the results indicate that 89.5% of the double bonds have been cleaved. Hydroxyl functionality, defined here as the average number of hydroxyl groups in 1 mole of triglyceride, was derived from the hydroxyl number (defined according to ASTM test method D1957-86 as the number of mg of potassium hydroxide equivalent to acetic anhydride consumed in the acetylation of 1 g of sample) was 5.2. The polyol product mixture was stable for 1 month at room temperature and no visible phase separation was observed.

Example 5

Soybean oil (200 g), ethylene glycol (150 g) and pyridine (35 gr) were placed in a 500 mL glass reactor and maintained at 0° C. in an ice/water bath under continuous stirring. Ozone was produced as described in Example 1 and was fed into the reactor through the fritted disc as small bubbles at a flow rate of 0.35 $ft^3$/min. The exhaust outlet from the reactor was connected to a potassium iodide aqueous solution trap in order to destroy excess ozone that has not been reacted. After 400 minutes reaction time, the ozone generator was switched off, the reaction mixture was allowed to warm up to room temperature and then washed with about 500 mL distilled water to remove any excess unreacted ethylene glycol and pyridine. The product was dried over molecular sieves for 48 hours.

The product mixture was characterized by FTIR and NMR and the results indicate that 79% of the double bonds have been cleaved. Hydroxyl functionality, defined here as the average number of hydroxyl groups in 1 mole of triglyceride, was derived from the hydroxyl number (defined according to ASTM test method D1957-86 as the number of mg of potassium hydroxide equivalent to acetic anhydride consumed in the acetylation of 1 g of sample) was 4.8. The polyol product mixture was stable for 1 month at room temperature and no visible phase separation was observed.

Example 6

Soybean oil (200 g), ethylene glycol (150 g) and 4-dimethylamino-pyridine (35 gr) were placed in a 500 mL glass reactor and maintained at 0° C. in an ice/water bath under continuous stirring. Ozone was produced as described in Example 1 and was fed into the reactor through the fritted disc as small bubbles at a flow rate of 0.35 ft$^3$/min. The exhaust outlet from the reactor was connected to a potassium iodide aqueous solution trap in order to destroy excess ozone that has not been reacted. After 400 minutes reaction time, the ozone generator was switched off, the reaction mixture was allowed to warm up to room temperature and then washed with about 500 mL distilled water to remove any excess unreacted ethylene glycol and 4-dimethylamino-pyridine. The product was dried over molecular sieves for 48 hours.

The product mixture was characterized by FTIR and NMR and the results indicate that 85% of the double bonds have been cleaved. Hydroxyl functionality, defined here as the average number of hydroxyl groups in 1 mole of triglyceride, was derived from the hydroxyl number (defined according to ASTM test method D1957-86 as the number of mg of potassium hydroxide equivalent to acetic anhydride consumed in the acetylation of 1 g of sample) was 5.1. The polyol product mixture was stable for 1 month at room temperature and no visible phase separation was observed.

Comparative Example 7

Soybean oil (200 g), ethylene glycol (150 g) and sodium hydroxide (30 gr) were placed in a 500 mL glass reactor and maintained at 0° C. in an ice/water bath under continuous stirring. Ozone was produced as described in Example 1 and was fed into the reactor through the fritted disc as small bubbles at a flow rate of 0.35 ft$^3$/min. The exhaust outlet from the reactor was connected to a potassium iodide aqueous solution trap in order to destroy excess ozone that has not been reacted. After a few minutes saponification (fatty acid salt formation) of the oil was observed and the reaction was terminated. This care might be taken not to saponify the oil with a strong base.

Example 8

Soybean oil (200 g), ethylene glycol (150 g) and magnesium oxide (35 gr) were placed in a 500 mL glass reactor and maintained at 0° C. in an ice/water bath under continuous stirring. Ozone was produced as described in Example 1 and was fed into the reactor through the fritted disc as small bubbles at a flow rate of 0.35 ft$^3$/min. The exhaust outlet from the reactor was connected to a potassium iodide aqueous solution trap in order to destroy excess ozone that has not been reacted. After 400 minutes reaction time, the ozone generator was switched off, the reaction mixture was allowed to warm up to room temperature and then washed with about 500 mL distilled water to remove any excess unreacted ethylene glycol. The MgO catalyst was then filtered out through a fine filter paper and the product was dried over molecular sieves for 48 hours.

The product mixture was characterized by FTIR and NMR and the results indicate that 88% of the double bonds have been cleaved. Hydroxyl functionality, defined here as the average number of hydroxyl groups in 1 mole of triglyceride, was derived from the hydroxyl number (defined according to ASTM test method D1957-86 as the number of mg of potassium hydroxide equivalent to acetic anhydride consumed in the acetylation of 1 g of sample) was 5.3. The polyol product mixture was stable for 1 month at room temperature and no visible phase separation was observed.

Example 9

Soybean oil (200 g), ethylene glycol (150 g) and triethylamine (35 gr) were placed in a 500 mL glass reactor and maintained at 0° C. in an ice/water bath under continuous stirring. Ozone was produced as described in Example 1 and was fed into the reactor through the fritted disc as small bubbles at a flow rate of 0.35 ft$^3$/min. The exhaust outlet from the reactor was connected to a potassium iodide aqueous solution trap in order to destroy excess ozone that has not been reacted. After 400 minutes reaction time, the ozone generator was switched off, the reaction mixture was allowed to warm up to room temperature and then washed with about 500 mL distilled water to remove any excess unreacted ethylene glycol and triethylamine. The product was dried over molecular sieves for 48 hours.

The product mixture was characterized by FTIR and NMR and the results indicate that 80% of the double bonds have been cleaved. Hydroxyl functionality, defined here as the average number of hydroxyl groups in 1 mole of triglyceride, was derived from the hydroxyl number (defined according to ASTM test method D1957-86 as the number of mg of potassium hydroxide equivalent to acetic anhydride consumed in the acetylation of 1 g of sample) was 4.8. The polyol product mixture was stable for 1 month at room temperature and no visible phase separation was observed.

Example 10

Soybean oil (200 g), ethylene glycol (150 g) and $CaCO_3$ (20 gr) were placed in a 500 mL glass reactor and maintained at 25° C. under continuous stirring. Ozone was produced as described in Example 1 and was fed into the reactor through the fritted disc as small bubbles at a flow rate of 0.35 ft$^3$/min. The exhaust outlet from the reactor was connected to a potassium iodide aqueous solution trap in order to destroy excess ozone that has not been reacted. After 400 minutes reaction time, the ozone generator was switched off, the reaction mixture was allowed to warm up to room temperature and then washed with about 500 mL distilled water to remove any excess unreacted ethylene glycol. The $CaCO_3$ catalyst was then filtered out through a fine filter paper and the product was dried over molecular sieves for 48 hours.

The product mixture was characterized by FTIR and NMR and the results indicate that 63% of the double bonds have been cleaved. Hydroxyl functionality, defined here as the average number of hydroxyl groups in 1 mole of triglyceride, was derived from the hydroxyl number (defined according to ASTM test method D1957-86 as the number of mg of potassium hydroxide equivalent to acetic anhydride consumed in the acetylation of 1 g of sample) was 4. The polyol product mixture was stable for 1 month at room temperature and no visible phase separation was observed.

Example 11

Soybean oil (200 g), low molecular weight polyethylene glycol (trade name PEG200, 150 g) and $CaCO_3$ (20 gr) were placed in a 500 mL glass reactor and maintained at 0° C. in an ice/water bath under continuous stirring. Ozone was produced as described in Example 1 and was fed into the reactor through the fritted disc as small bubbles at a flow rate of 0.35 $ft^3$/min. The exhaust outlet from the reactor was connected to a potassium iodide aqueous solution trap in order to destroy excess ozone that has not been reacted. After 400 minutes reaction time, the ozone generator was switched off, the reaction mixture was allowed to warm up to room temperature and then washed with about 500 mL distilled water to remove any excess unreacted ethylene glycol. The $CaCO_3$ catalyst was then filtered out through a fine filter paper and the product was dried over molecular sieves for 48 hours.

The product mixture showed large hydroxyl absorption in the FTIR spectrum and only residual double bonds functionality. It was stable for 1 month at room temperature with no visible phase separation and was formulated into flexible polyurethane foam.

Example 12

Soybean oil (200 g), medium molecular weight polyethylene glycol (trade name PEG400, 150 g) and $CaCO_3$ (20 gr) were placed in a 500 mL glass reactor and maintained at 0° C. in an ice/water bath under continuous stirring. Ozone was produced as described in Example 1 and was fed into the reactor through the fritted disc as small bubbles at a flow rate of 0.35 $ft^3$/min. The exhaust outlet from the reactor was connected to a potassium iodide aqueous solution trap in order to destroy excess ozone that has not been reacted. After 400 minutes reaction time, the ozone generator was switched off, the reaction mixture was allowed to warm up to room temperature and then washed with about 500 mL distilled water to remove any excess unreacted ethylene glycol. The $CaCO_3$ catalyst was then filtered out through a fine filter paper and the product was dried over molecular sieves for 48 hours.

The product mixture showed large hydroxyl absorption in the FTIR spectrum and only residual double bonds functionality. It was stable for 1 month at room temperature with no visible phase separation and was formulated into flexible polyurethane foam.

Example 13

Soybean oil (200 g), high molecular weight polyethylene glycol (trade name PEG600, 150 g) and $CaCO_3$ (20 gr) were placed in a 500 mL glass reactor and maintained at 0° C. in an ice/water bath under continuous stirring. Ozone was produced as described in Example 1 and was fed into the reactor through the fritted disc as small bubbles at a flow rate of 0.35 $ft^3$/min. The exhaust outlet from the reactor was connected to a potassium iodide aqueous solution trap in order to destroy excess ozone that has not been reacted. After 400 minutes reaction time, the ozone generator was switched off, the reaction mixture was allowed to warm up to room temperature and then washed with about 500 mL distilled water to remove any excess unreacted ethylene glycol. The $CaCO_3$ catalyst was then filtered out through a fine filter paper and the product was dried over molecular sieves for 48 hours.

The product mixture showed large hydroxyl absorption in the FTIR spectrum and only residual double bonds functionality. It was stable for 1 month at room temperature with no visible phase separation and was formulated into flexible polyurethane foam.

Comparative Example 14

Soybean oil (200 g), ethylene glycol (150 g) and no catalyst were placed in a 500 mL glass reactor and maintained at 0° C. in an ice/water bath under continuous stirring. Ozone was produced as described in Example 1 and was fed into the reactor through the fritted disc as small bubbles at a flow rate of 0.35 $ft^3$/min. The exhaust outlet from the reactor was connected to a potassium iodide aqueous solution trap in order to destroy excess ozone that has not been reacted. After 400 minutes reaction time, the ozone generator was switched off, the reaction mixture was allowed to warm up to room temperature and then washed with about 500 mL distilled water to remove any excess unreacted ethylene glycol and the product was dried over molecular sieves for 48 hours.

The product mixture was characterized by FTIR and the results indicate that it contains a mixture of various carboneceous compounds primarily aldehydes and carboxylic acids. The mixture separated into two (2) phases within 1 week when left undisturbed at room temperature.

It is intended that the foregoing description be only illustrative of the present invention and that the present invention be limited only by the hereinafter appended claims. Because other modifications and changes varied to fit particular operating requirements and environments will be apparent to those skilled in the art, the disclosure is not considered limited to the examples chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

Throughout the specification, where the compositions, processes/methods, or apparatus are described as including components, steps, or materials, it is contemplated that the compositions, processes/methods, or apparatus can also comprise, consist essentially of, or consist of, any combination of the disclosed components or materials, unless described otherwise. Component concentrations expressed as a percent are weight-percent (% w/w), unless otherwise noted. Numerical values and ranges can represent the value/range as stated or an approximate value/range (e.g., modified by the term "about"). Combinations of components are contemplated to include homogeneous and/or heterogeneous mixtures, as would be understood by a person of ordinary skill in the art in view of the foregoing disclosure.

What is claimed is:
1. A method for making a modified fatty acid ester, the method comprising:
   (a) reacting an unsaturated fatty acid ester with ozone in a reaction mixture in the presence of a hydroxylated compound and an alkaline catalyst to form a reaction product,
   wherein:

(i) the ozone and the unsaturated fatty acid ester react to cleave double bonds in fatty acid groups of the unsaturated fatty acid ester, and (ii) the hydroxylated compound, in the presence of the alkaline catalyst, is added to terminal carbons of the cleaved double bonds through an ester covalent bond.

2. The method of claim 1, wherein the unsaturated fatty acid ester comprises a natural oil triglyceride.

3. The method of claim 2, wherein the natural oil triglyceride comprises an animal oil triglyceride.

4. The method of claim 3, wherein the animal oil triglyceride comprises fish oil.

5. The method of claim 2, wherein the natural oil triglyceride comprises a vegetable oil triglyceride, the vegetable oil triglyceride comprising one or more of soybean oil, safflower oil, linseed oil, corn oil, sunflower oil, olive oil, canola oil, sesame oil, cottonseed oil, palm oil, peanut oil, coconut oil, rapeseed oil, tung oil, and castor oil.

6. The method of claim 1, wherein the hydroxylated compound has at least two hydroxyl groups.

7. The method of claim 6, wherein the hydroxylated compound comprises one or more of glycols, linear polyols, glycerin, trimethylol propane, pentaerythritol, glucosides, sugars, and catechols.

8. The method of claim 6, wherein the hydroxylated compound comprises one or more of ethylene glycol, 1,2-propylene glycol, 1,3-propylene glycol, 1,2-butylene glycol, 1,3-butylene glycol, 1,4-butylene glycol, 1,2-pentylene glycol, 1,3-pentylene glycol, 1,4-pentylene glycol, 1,5-pentylene glycol, neopentyl glycol, and hexane diols.

9. The method of claim 1, wherein the hydroxylated compound comprises a mono-alcohol.

10. The method of claim 9, wherein the mono-alcohol comprises one or more of a linear hydrocarbon chain, a branched hydrocarbon chain, and combinations thereof.

11. The method of claim 1, wherein the alkaline catalyst comprises one or more of an alkali metal hydroxide, an organic amine, a salt derived from a strong base and a weak acid, and a metal oxide having an alkaline surface.

12. The method of claim 1, wherein the reaction product comprises:

(a) a modified fatty acid ester comprising: an ester of an alkaline-catalyzed, ozone-cleaved unsaturated fatty acid ester comprising a terminal carbon atom, wherein the terminal carbon atom is covalently linked through an ester reaction product of (i) the alkaline-catalyzed, ozone-cleaved unsaturated fatty acid and (ii) the a hydroxylated compound.

13. The method of claim 12, wherein the reaction product further comprises:

(b) one or more of diesters and monoesters resulting from the reaction of the hydroxylated compound with cleaved portions of the fatty acid groups of the fatty acid ester.

14. A composition derived from a fatty acid ester, the composition comprising:

(a) a modified fatty acid ester comprising: an ester of an alkaline-catalyzed, ozone-cleaved unsaturated fatty acid ester comprising a terminal carbon atom, wherein the terminal carbon atom is covalently linked through an ester reaction product of (i) the alkaline-catalyzed, ozone-cleaved unsaturated fatty acid and (ii) the hydroxylated compound.

15. The composition of claim 14, wherein the unsaturated fatty acid ester comprises a natural oil triglyceride.

16. The composition of claim 15, wherein the modified fatty acid ester comprises more than three ester groups per triglyceride molecule.

17. The composition of claim 14, wherein the hydroxylated compound has at least two hydroxyl groups.

18. The composition of claim 17, wherein the modified fatty acid ester comprises primary alcohol groups.

19. The composition of claim 14, wherein the hydroxylated compound comprises a mono-alcohol.

20. The composition of claim 14, further comprising: (b) one or more of diesters and monoesters resulting from the reaction of the hydroxylated compound with cleaved portions of the fatty acid groups of the fatty acid ester.

21. A method of making a natural oil-based primary polyol, the method comprising ozonizing a natural oil in the presence of a polyol and an alkaline catalyst.

22. The composition of claim 15, wherein the natural oil triglyceride comprises a vegetable oil triglyceride, the vegetable oil triglyceride comprising one or more of soybean oil, safflower oil, linseed oil, corn oil, sunflower oil, olive oil, canola oil, sesame oil, cottonseed oil, palm oil, peanut oil, coconut oil, rapeseed oil, tung oil, and castor oil.

* * * * *